(12) United States Patent
Tenerz et al.

(10) Patent No.: US 7,044,916 B2
(45) Date of Patent: May 16, 2006

(54) TECHNIQUE TO CONFIRM CORRECT POSITIONING OF ARTERIAL WALL SEALING DEVICE

(75) Inventors: Lars Tenerz, Uppsala (SE); Dan Åkerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/704,556

(22) Filed: Nov. 12, 2003

(65) Prior Publication Data

US 2004/0098046 A1 May 20, 2004

Related U.S. Application Data

(62) Division of application No. 10/042,247, filed on Jan. 11, 2002, now Pat. No. 6,682,489.

(51) Int. Cl.
*A61B 5/02* (2006.01)
*A61B 17/08* (2006.01)
*A61B 17/04* (2006.01)

(52) U.S. Cl. ............ 600/485; 600/481; 606/231; 606/214

(58) Field of Classification Search ......... 600/481, 600/488, 485, 486; 606/213–215, 139, 144, 606/148, 264

See application file for complete search history.

(56) References Cited

U.S. PATENT DOCUMENTS

| | | | |
|---|---|---|---|
| 4,834,108 A * | 5/1989 | Vaillancourt | 600/486 |
| 4,852,568 A * | 8/1989 | Kensey | 606/213 |
| 4,890,612 A * | 1/1990 | Kensey | 606/213 |
| 5,222,974 A * | 6/1993 | Kensey et al. | 606/213 |
| 5,431,639 A | 7/1995 | Shaw | |
| 5,613,974 A | 3/1997 | Andreas et al. | |
| 5,766,206 A * | 6/1998 | Wijkamp et al. | 606/213 |
| 5,855,559 A | 1/1999 | Van Tassel et al. | |
| 5,861,004 A * | 1/1999 | Kensey et al. | 606/213 |
| 5,964,782 A | 10/1999 | Lafontaine et al. | |
| 6,007,563 A | 12/1999 | Nash et al. | |
| 6,090,130 A | 7/2000 | Nash et al. | |
| 6,117,144 A * | 9/2000 | Nobles et al. | 606/144 |
| 6,193,670 B1 | 2/2001 | Van Tassel et al. | |
| 6,302,898 B1 * | 10/2001 | Edwards et al. | 606/214 |

(Continued)

FOREIGN PATENT DOCUMENTS

WO WO 98/07372 A2 2/1998

(Continued)

*Primary Examiner*—Robert L. Nasser
*Assistant Examiner*—Navin Natnithithadha
(74) *Attorney, Agent, or Firm*—Foley & Lardner LLP

(57) ABSTRACT

Methods and systems related to sealing punctures in blood vessels (such as following an angio or PTCA procedure) are disclosed. The position of a distal end of an introducer assembly in tissue is determined using a pressure sensor. The pressure sensor is connected to the proximal end of the introducer assembly. The introducer assembly has a fluid path between its distal end and its proximal end. Measured blood pressure is outputted as an indication of the position of the distal end of the introducer assembly in the tissue. Proper positioning of a seal is confirmed by placing the introducer assembly such that its distal end is in tissue outside a puncture in a blood vessel wall and observing a characteristic of blood at the proximal end of the introducer assembly. In both techniques, a waveform of the blood pressure at the distal end of the introducer assembly may be displayed on a display to provide additional information to a surgeon as to the relative position of the components with respect to various tissues.

6 Claims, 5 Drawing Sheets

U.S. PATENT DOCUMENTS

| | | |
|---|---|---|
| 6,350,274 B1 * | 2/2002 | Li .............................. 606/213 |
| 6,508,828 B1 | 1/2003 | Akerfeldt et al. |
| 6,682,489 B1 * | 1/2004 | Tenerz et al. ................ 600/485 |
| 6,733,515 B1 * | 5/2004 | Edwards et al. ............ 606/214 |

FOREIGN PATENT DOCUMENTS

| | | |
|---|---|---|
| WO | WO 98/19605 A1 | 5/1998 |
| WO | WO 98/40016 A2 | 9/1998 |

* cited by examiner

TECHNIQUE TO CONFIRM CORRECT POSITIONING OF ARTERIAL WALL SEALING DEVICE

CROSS-REFERENCE TO RELATED PATENT APPLICATIONS

The present application is a divisional of U.S. application Ser. No. 10/042,247, filed Jan. 11, 2002, now U.S. Pat. No. 6,682,489 the entire contents of which are incorporated herein by reference. The Applicants hereby claim the benefit of priority of U.S. Provisional Patent Application No. 60/260,895, filed Jan. 12, 2001. The entire contents of this provisional application are incorporated herein by reference.

BACKGROUND OF THE INVENTION

The invention relates to sealing punctures in tissues of living bodies. The invention can be used, for example, when sealing punctures in the walls of arteries (such as following an angio or PTCA procedure) or other blood vessels. Background and various details of such techniques can be found in U.S. patent application Ser. No. 09/704,726 entitled "Sealing Device and Wound Closure Device" and filed on Nov. 3, 2000 by Dan Akerfeldt et al; U.S. Pat. No. 5,613,974 (Assigned to Perclose, Inc.); and U.S. Pat. No. 6,090,130 (assigned to Kensey Nash Corporation). The entire contents of this application and these two patents are incorporated herein by reference.

In the course of using sealing devices or anchors that are inserted into an artery, it is helpful to detect the position of the various components with respect to the arterial wall. If an introducer is positioned based on feeling, there is a risk that the introducer pops out from the artery, and it is almost impossible to reintroduce it in an easy way. Ideally, the seal or anchor is deployed as close to the puncture hole as possible. If the seal or anchor is deployed too deep in the artery, the risk increases that the seal or anchor will be caught upstream in the artery before being seated on the puncture hole and/or cause injury to the inside of the artery wall.

An introducer is normally 10–15 cm long, and during cauterization it is fully inserted. To seal the puncture hole, a seal needs to have a diameter larger than the introducer, e.g. >3 mm. To be properly seated to the inside of the artery hole, the seal needs to be even larger, otherwise the seal may be pulled out by mistake. The femoral artery inside diameter is normally 5–10 mm in humans, and it is difficult to increase the seal width to more than 5 mm because, if the seal width is bigger, it is difficult to fit the seal into the arterial lumen without affecting the circularity of the lumen too much. The length of the seal can however be increased to achieve high pull out strength.

The FemoSeal seal (described in Ser. No. 09/704,726) and Kensey Nash AngioSeal anchors described in U.S. Pat. No. 6,090,130) have a length of 10 mm, and consequently can get caught perpendicular in the 5–10 mm arterial lumen if the position and direction of the seal or anchor inserted in the artery are not guided. As discussed above, the seal or anchor can also be caught in an artery branch upstream. The AngioSeal technique employs an anchor that can move around in the artery as its inner member. The anchor does not perform a sealing function (and is not a "seal" as this term is used in this patent specification) but instead anchors an outer member and the outer member performs the sealing function. The AngioSeal technique solves the problem of detecting the position of the various components relative to the vessel wall by detecting the vessel wall by introducing an indicator through the introducer. This is a tube that extends 3 cm distal of the introducer tip with a side hole positioned 1 mm distal from the introducer tip. By pulling the introducer back and forth, the tip can be positioned at a desired position from the vessel wall by looking at blood dripping out from the indicator. This can be done without losing the entrance into the artery. Then, the anchor can be deployed near the puncture hole, 1 cm upstream, and the risk of getting the anchor caught upstream is reduced.

A technique used by Perclose (described in U.S. Pat. No. 5,613,974) is similar in that a channel through the device, with a side hole, is provided to visually detect blood emerging from the device handle to indicate the device position within the artery.

SUMMARY OF THE INVENTION

The invention addresses and solves two problems which occur in the sealing of punctures in blood vessels. The first problem is to detect the arterial wall in order to position the introducer tip at the correct location inside the vessel.

A second problem is to confirm that an inner seal itself is correctly positioned and is performing its sealing function.

In preferred embodiments of the invention, the position of a distal end of an introducer assembly in tissue is determined using a pressure sensor. The pressure sensor is connected to the proximal end of the introducer assembly. The introducer assembly has a fluid path between its distal end and its proximal end. Measured blood pressure is outputted as an indication of the position of the distal end of the introducer assembly in the tissue. Proper positioning of an inner seal is confirmed by placing the introducer assembly such that its distal end is in tissue outside a puncture in a blood vessel wall and observing a characteristic of blood at the proximal end of the introducer assembly. In both techniques, a waveform of the blood pressure at the distal end of the introducer assembly may be displayed on a display to provide additional information to a surgeon as to the relative position of the components with respect to various tissues.

A pressure transducer is not needed to confirm that the puncture is sealed, since the flow of blood can be observed from an output port in the introducer if the puncture is not sealed. The output port can be, for example, a hole in the proximal end of the introducer, a clear tube connected to the proximal end of the introducer, or the like. However, providing a pressure transducer, or a similar device, allows generation of pressure waveforms and thus provides additional information to the surgeon.

DETAILED DESCRIPTION OF PREFERRED EMBODIMENTS

Figure 1:
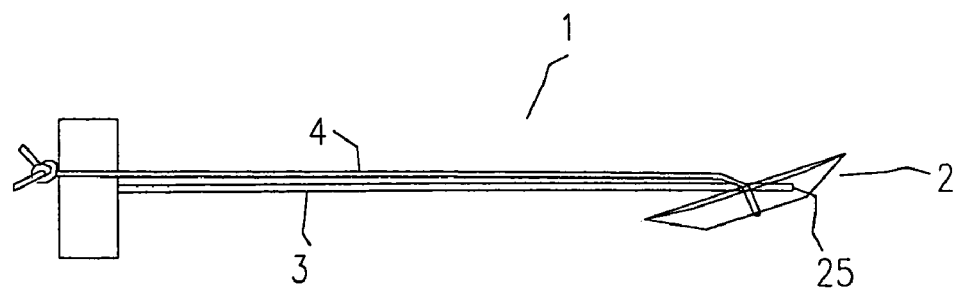
FIGS. 1 to 7 illustrate the design and operation of a first embodiment of the invention.

The invention provides an improved technique to detect the position of an introducer assembly in a blood vessel. According to this technique, the invention electronically (or optically) quantitatively measures the presence, amount (for example, absolute pressure), and/or waveform of blood pressure in the introducer, as opposed to visually detecting the presence of blood, as in the prior art. To accomplish this, a standard bedside blood pressure transducer is connected to the introducer's sidearm and the pressure (in for example mmHg) is displayed on a lab monitor.

The invention also provides a technique to detect the proper sealing of a puncture in a blood vessel wall. In this technique, after deploying an inner seal, the blood pressure in the tissue immediately outside of the seal is measured. If the puncture is not sealed (if, for example, the inner seal is caught upstream), significant blood pressure will still be indicated, and the seal can then be manipulated and twisted until it is released in the artery and can then be positioned properly.

When the inner seal is properly seated, the blood pressure will disappear. If the sealing is incomplete, a pressure will still be present, but at a lower level, and this indicates the need for, for example, harder tightening of the sealing elements.

The measured pressure waveform is displayed on the monitor to give the surgeon information as to the positioning of the various components relative to one another and relative to the various tissues. In addition, the pressure waveform can be analyzed electronically to provide the surgeon with further information.

Thus, the invention provides information regarding whether the introducer tip is in the artery, in the vessel wall, or outside the vessel. After closure of the puncture, the pressure information provided by the invention indicates if the inner seal is tight or leaks. A small leak from the artery can be distinguished from tissue oozing by observing and/or analyzing the pressure waveform (for example, a pulsed waveform shape suggests a small leak). An artery leak indicates the need for better tightening of the seal. Tissue oozing requires no further action.

In a puncture closure device that has a seal inside the artery and a seal outside the artery (such as the FemoSeal seal), the invention can serve additional purposes. After deployment of the inner seal in the artery, the device is withdrawn until a resistance is felt. At that point, the inner seal should be seated over the inside of the puncture and the outer seal can then be deployed without risk of being deployed inside the artery. If the inner seal is caught upstream in the artery, without the invention, the surgeon may misinterpret the resistance (when the device is pulled) as an indication that the inner seal is seated over the puncture hole. However, with the invention, the fact that the inner seal is caught upstream in the artery will be detected by reading the pressure on the monitor.

FIGS. 1 to 10 illustrate various embodiments of the invention. These figures illustrate use of the invention in conjunction with the FemoSeal seal. However, the invention can be used in connection with a wide variety of seals other than the FemoSeal seal.

Figure 2:
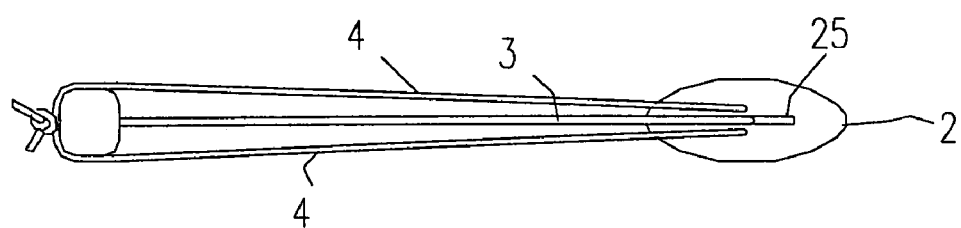
Figure 3:
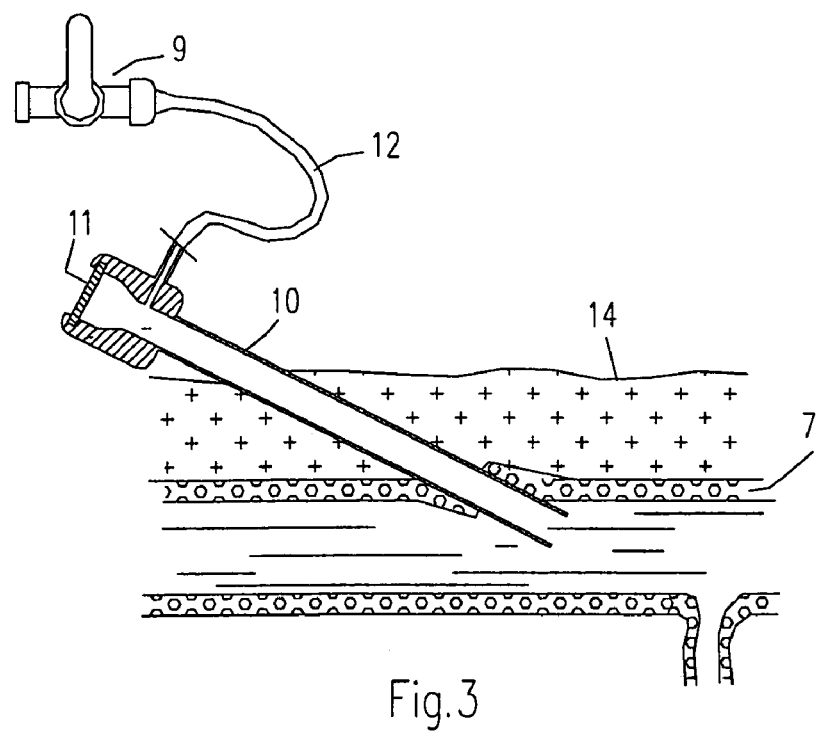

FIGS. 1 and 2 illustrate an apparatus 1 having an inner seal 2, a pusher 3 (with a tip 25), and a suture 4. FIG. 3 illustrates a sidearm 9 (with a stopcock in a closed position), an introducer 10, a hemostatic valve 11, and a tube 12, positioned with respect to artery wall 7 in tissue 14. Inner seal 2 performs two distinct functions. First, inner seal 2 seals the puncture in the blood vessel wall. Second, seal 2 holds an outer seal (not shown) in place. The above-identified patent application describes these components in further detail.

Figure 4:
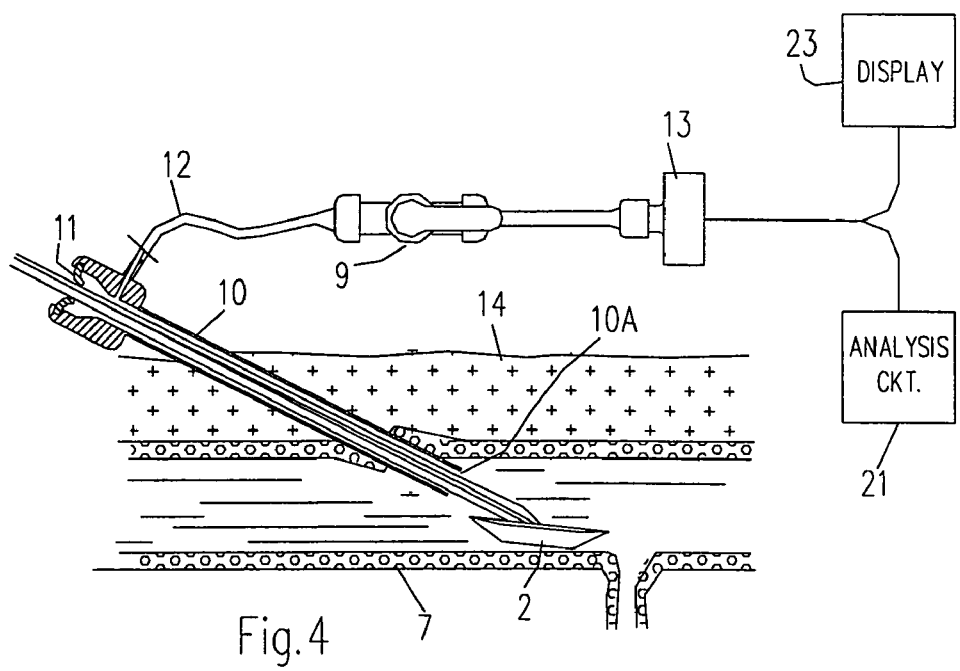

FIG. 4 shows inner seal 2 deployed within the artery, sidearm 9 (with a stopcock in an open position), and a pressure transducer 13. The pressure transducer 13 is in fluid communication with the distal tip 10A of introducer 10.

Thus, in FIG. 4, transducer 13 senses normal arterial pressure. The pressure transducer can be any pressure transducer suitable for measuring blood pressure.

FIG. 4 also shows a display 23 to display pressure waveforms to the surgeon. The display can be any type of display or monitor. An analysis circuit 21 is also provided, which analyses the pressure data to output additional information to the surgeon.

Figure 5:
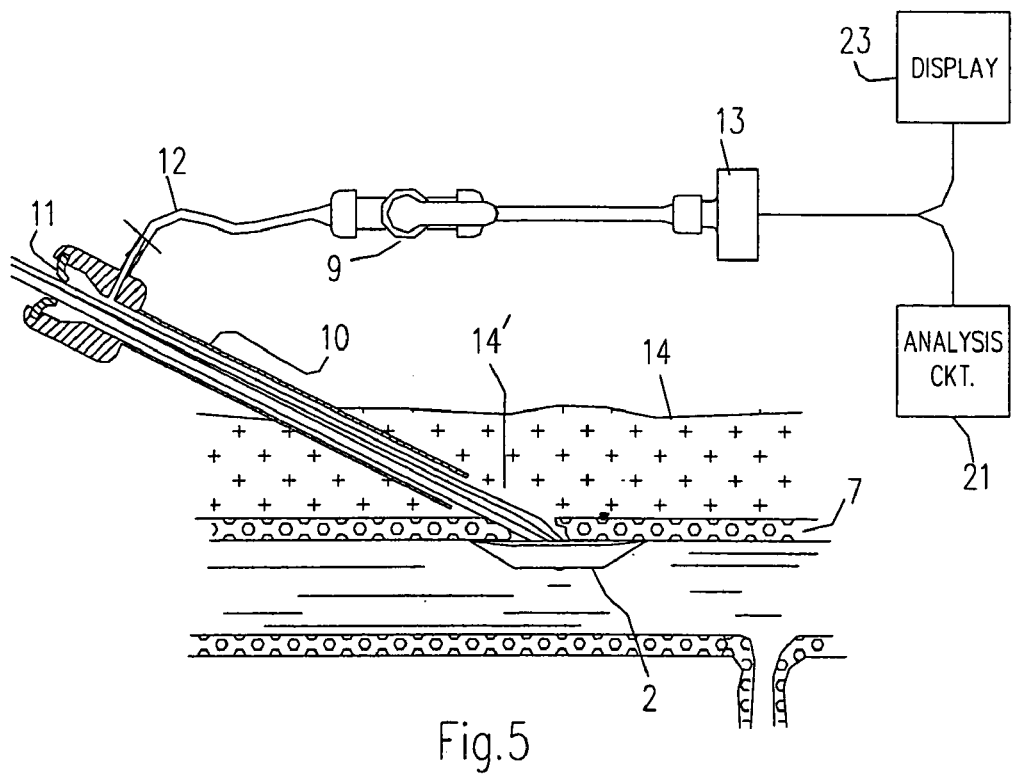

FIG. 5 shows the inner seal 2 properly seated to a puncture hole. In FIG. 5, transducer 13 senses essentially no normal arterial pressure and no normal pressure waveforms in the tissue 14' immediately outside of the seal. Thus, by monitoring the pressure (actually lack of pressure) via transducer 13, display 23, and/or analysis circuit 21, the surgeon can confirm that seal 2 is properly seated (that is, that seal 2 mates with the inner wall of the blood vessel in a leak tight fashion). If the sealing were incomplete, a pressure will still be present, but at a lower level, and this indicates the need for harder tightening of the sealing elements. The technique shown in FIG. 5 can also be employed to determine whether a seal which seals the puncture from outside the artery is properly positioned.

Figure 6:
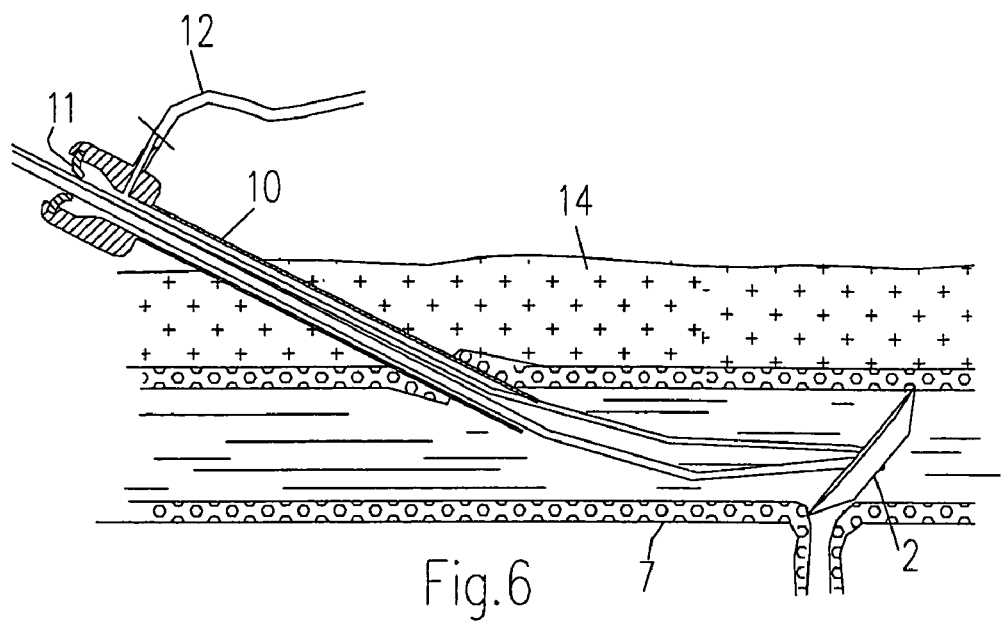

FIG. 6 shows seal 2 caught in an upstream branch. As described above, if the seal is caught upstream, blood pressure will still be indicated on the display (or monitor), and the seal can then be manipulated and twisted until it is released from the branch and can be seated to the puncture hole. In the FIG. 6 situation, when the surgeon pulls on sutures 4, the surgeon feels significant resistance and may wrongly believe (without use of the invention) that the seal is properly seated.

Figure 7:
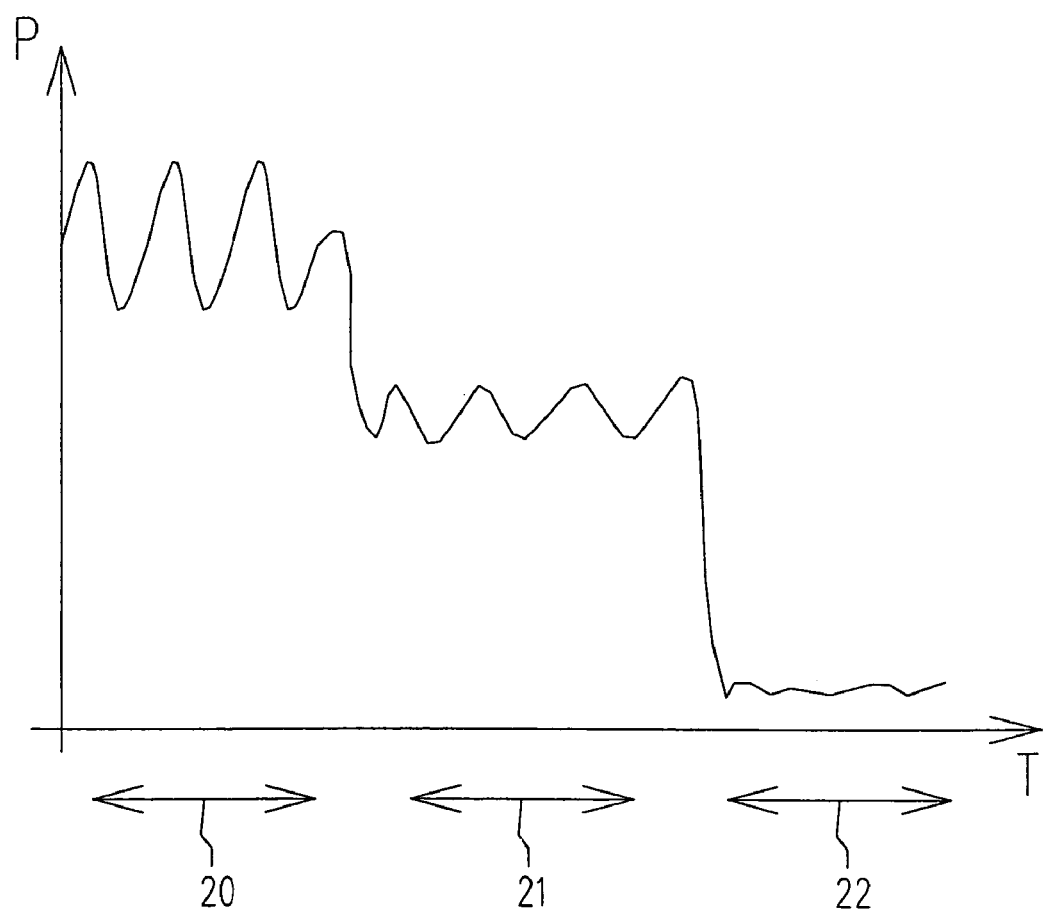

FIG. 7 illustrates examples of waveforms displayed on display 23. Waveform 20 corresponds to the situation when an inner seal is inside the blood vessel and an introducer is positioned as shown in FIG. 4. Waveform 22 corresponds to the situation when the inner seal is positioned as shown in FIG. 5. Waveform 21 corresponds to the situation when the sealing is incomplete.

Figure 8:
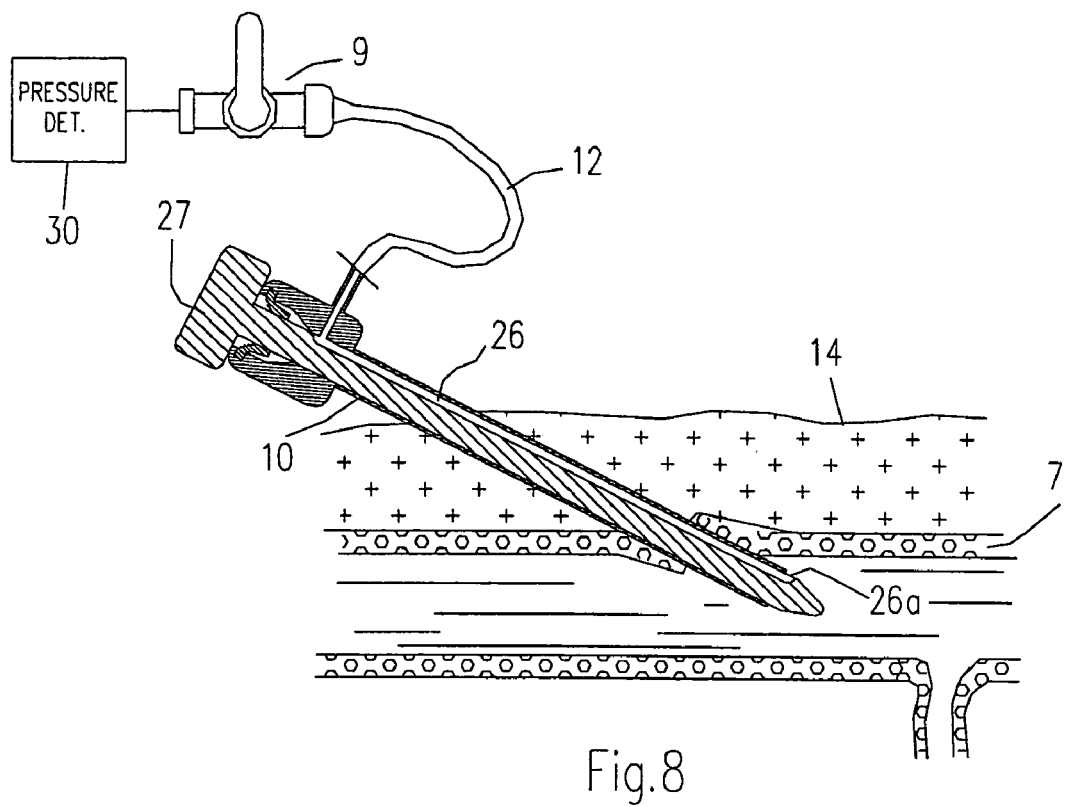
FIG. 8 illustrates a second embodiment of the invention.
Figure 9:
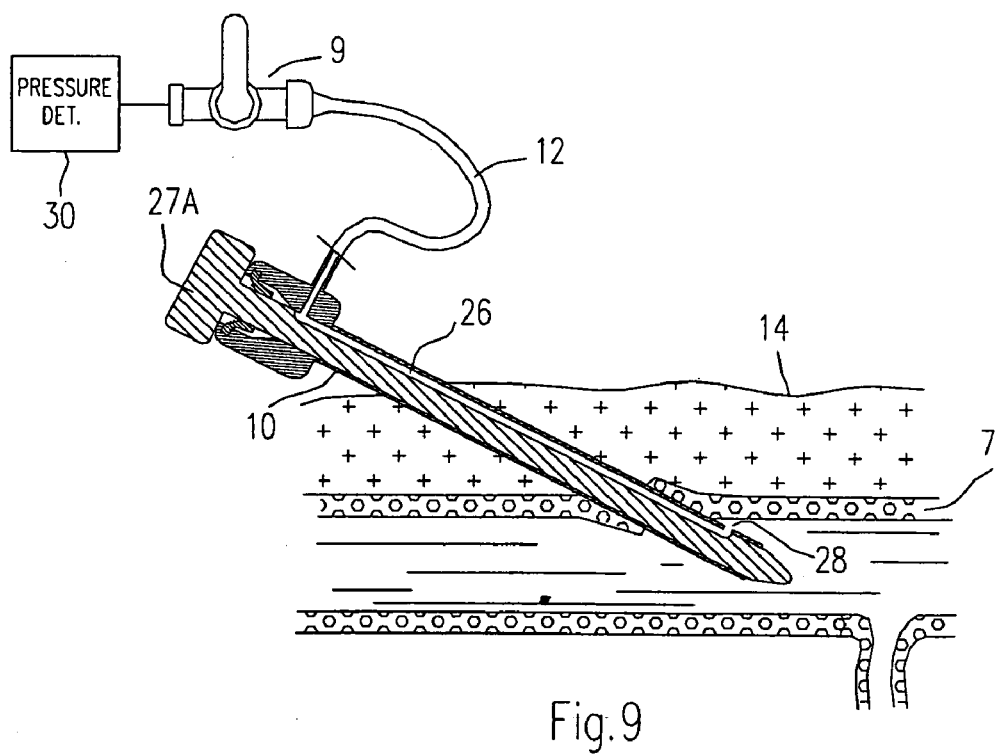
FIG. 9 illustrates a third embodiment of the invention.
Figure 10:
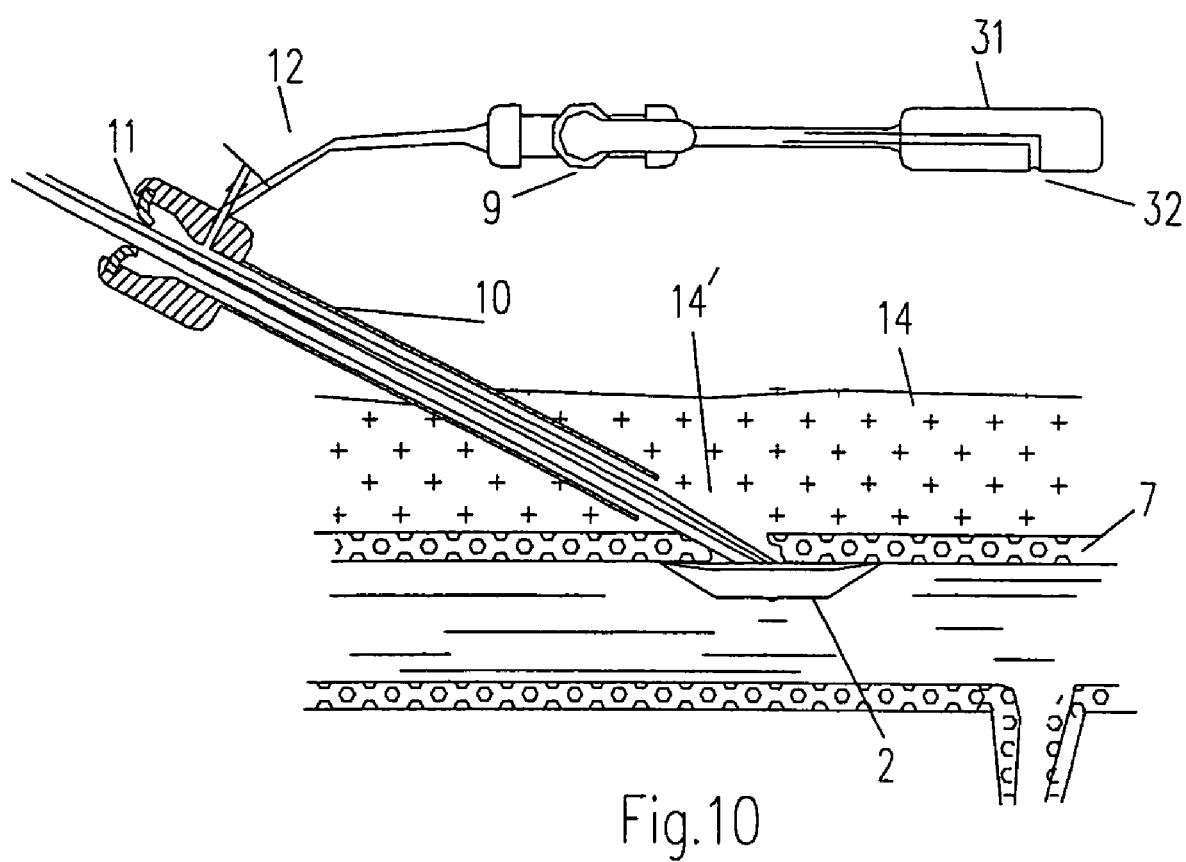
FIG. 10 illustrates a fourth embodiment of the invention.

FIGS. 8, 9, and 10 show second, third, and fourth embodiments of the invention.

FIG. 8 shows an introducer 10 with a core pin 27 inserted. The core pin (a dilator) has one channel 26 (or an axial grove) that communicates a tip opening 26a with the sidearm 9. With this technique, the introducer is pushed/pulled forward and backward until the opening 26a (or sidehole) is sealed by the vessel wall 7. This can be detected by a loss of pressure with pressure detector 30. The detector 30 is similar to transducer 13 and equipped with a display or audible indication of pressure, for example, an audible indication which varies as pressure varies. The detector is connectable, or adaptable, to the sidearm 9. Once it is confirmed that the introducer tip is positioned at the wall, the introducer can then be pushed forward into the vessel to a desired length. Then, the seal can be inserted into the introducer and deployed as close to the puncture site as possible.

FIG. 9 shows an introducer 33 with a core pin 27A inserted. The introducer has a sidehole 28 at a desired distance from the tip. With this design, the introducer can be positioned in a single operation by monitoring the pressure on detector 30, and the length that the introducer protrudes into the vessel is defined by the length from the sidehole to the introducer tip. For example, the introducer can be positioned by positioning hole 28 just inside the vessel wall by monitoring pressure on detector 30.

The technique shown in FIG. 10 is similar to the technique shown in FIG. 5, except that in FIG. 10, proper sealing of the inner seal 2 is determined by observing the absence of blood flow from an output port (or drip channel) 32 in an attachment 31.

The invention is, of course, not limited to these specific embodiments. Modifications and variations of the invention will occur to those skilled in the field, after receiving the above teachings. The invention is therefore defined by reference to the following claims.

What is claimed is:

1. A method to detect sealing of a puncture in a blood vessel wall by a seal inside a blood vessel, comprising:
   (a) providing an introducer assembly having a distal end and a proximal end and a fluid path between the distal end and the proximal end;
   (b) placing the introducer assembly such that the distal end of the introducer assembly is inside a blood vessel;
   (c) placing a seal against an inner wall of the blood vessel by deploying the seal inside the blood vessel and then retracting the seal until contact with the inner wall of the blood vessel;
   (d) placing the introducer assembly such that the distal end of the introducer assembly is outside the inner wall of the blood vessel; and
   (e) determining whether the puncture is sealed by said seal by observing a characteristic of blood at the proximal end of the introducer assembly.

2. A method as set forth in claim 1, wherein step (e) includes:
   visually observing a flow of blood at the proximal end of the introducer assembly.

3. A method as set forth in claim 1, wherein step (e) includes
   measuring blood pressure at the proximal end of the introducer assembly with a pressure sensor and outputting an indication of measured blood pressure.

4. A method as set forth in claim 1, wherein step (e) includes
   measuring blood pressure at the proximal end of the introducer assembly with a pressure sensor and displaying a numerical indication of measured blood pressure.

5. A method as set forth in claim 1, wherein step (e) includes
   measuring blood pressure at the proximal end of the introducer assembly with a pressure sensor; and
   displaying a blood pressure waveform on a display.

6. A method as set forth in claim 1, further comprising:
   after step (c), placing a seal outside the blood vessel.

* * * * *